United States Patent

Perusse

[11] Patent Number: 5,913,556
[45] Date of Patent: Jun. 22, 1999

[54] CONTACT LENS APPLICATOR

[76] Inventor: Mel Perusse, 677 Cathedral Avenue, Winnipeg, Manitoba, Canada, R2W 0Y9

[21] Appl. No.: 09/055,763

[22] Filed: Apr. 7, 1998

[51] Int. Cl.[6] ...................................................... A61F 9/00
[52] U.S. Cl. .............................................. 294/1.2; 294/25
[58] Field of Search ........................... 294/1.2, 25, 64.1; 206/5.1; 606/107

[56] References Cited

U.S. PATENT DOCUMENTS

| | | | |
|---|---|---|---|
| 1,316,436 | 9/1919 | Feeney | 294/25 |
| 3,031,918 | 5/1962 | Moyers | 294/1.2 |
| 3,132,887 | 5/1964 | Martinez | 294/1.2 |
| 3,139,298 | 6/1964 | Grabiel | 294/1.2 |
| 3,490,806 | 1/1970 | Lopez-Calleja et al. | 294/1.2 |
| 4,167,283 | 9/1979 | Feldman | 294/1.2 |
| 4,387,921 | 6/1983 | Licata | 294/1.2 |
| 4,479,672 | 10/1984 | Jermyn | 294/1.2 |
| 5,649,727 | 7/1997 | St. Louis | 294/1.2 |

FOREIGN PATENT DOCUMENTS

| 3822654 | 1/1990 | Germany | 294/1.2 |
|---|---|---|---|

*Primary Examiner*—Johnny D. Cherry
*Attorney, Agent, or Firm*—Murray E. Thrift; A. Battison

[57] ABSTRACT

A contact lens applicator is used in inserting a contact lens into an eye. The applicator includes a stem with a finger mount on one end for mounting the applicator on a finger, and a contact lens retainer on the other end. In use the contact lens applicator is secured on the finger of the person adjacent the fingertip by the finger mount and a contact lens is placed on the contact lens retainer. The contact lens is oriented on the retainer transverse to and offset from the finger tip. The retainer holds the contact lens in place as the finger is moved into a substantially horizontal position with the contact lens positioned forward of the fingertip and oriented vertically. This allows the contact lens to be inserted into the eye easily and without tilting the head downwards. It enables a person to hold the top and bottom eyelids open using the fingers of both hands. The contact lens is inserted into the eye by moving the applicator towards the eye until the lens lightly touches the eye, which releases the lens.

6 Claims, 3 Drawing Sheets

CONTACT LENS APPLICATOR

FIELD OF THE INVENTION

The present invention relates to a contact lens applicator for placing a contact lens in a wearer's eye.

BACKGROUND

Individuals who use contact lenses must regularly perform the task of placing a contact lens into each eye. The most common method of inserting a contact lens involves bathing the contact lens in a saline or other sterile lubricating solution, placing the contact lens on a fingertip and placing the lens onto the eye with the supporting finger. To do this the finger is placed under the contact lens to support the contact lens and the face of the individual is tilted downwards. At the same time, the eyelids of the eye receiving the lens are held open and the contact lens is lifted into the eye.

This technique has a number of problems. Firstly, it is difficult to see the contact lens when the finger is brought close to the eye since the image of the finger obscures the image of the lens. Secondly, since the wet contact lens merely rests upon the fingertip, the fingertip must be arranged to support the contact lens from below and thus requires that the face of the individual be tilted downwards when placing the contact lens in the eye. If the contact lens is not supported from below, it will tend to slide off of the fingertip as the individual attempts to insert it. This makes it difficult for an individual to use a mirror when inserting the contact lens to overcome the problem of having difficulty seeing the contact lens. Furthermore, having the head tilted downwards and balancing the contact lens on the fingertip is awkward and makes the task of placing a contact lens in the eye more difficult. Thirdly placing the contact lens in the eye with a fingertip can result in oils, dust, make-up, or other materials getting onto the contact lens which can cause contamination of the eye resulting in discomfort and in extreme cases infection.

One known device for applying a contact lens to the eye of an individual, is taught by Arthur C. Jermyn in U.S. Pat. No. 4,479,672 Oct. 30, 1984 entitled "Contact Lens Inserter". Jermyn teaches a contact lens inserter comprising a handle and a cup shaped portion for retaining the contact lens thereon. The handle is held between the thumb and a finger of one hand. The handle is angled at the end, which displaces the fingers from the line of sight to the contact lens so that the image of the finger does not obscure the image of the contact lens. The contact lens is retained on the cup portion while the person places the contact lens in the eye. This allows the person to insert the contact lens with the head in an upright position. This device however has the disadvantage that it requires the use of the thumb and finger of one hand to hold the handle when placing the contact lens in the eye. Positioning the inserter while holding it between the thumb and finger is more difficult than simply moving a single fingertip to the eye. In addition, holding the inserter between the thumb and finger of one hand requires that the fingers of the other hand hold open both the top and bottom eyelids which is also awkward.

SUMMARY

According to the present invention there is provided a contact lens applicator for applying a contact lens to an eye of a person using a finger of the person, said finger having a fingertip, said contact lens applicator comprising:

an elongate stem;

a contact lens retaining means on a first end of the stem for retaining a contact lens on the end of the stem, with the lens transverse to the stem end: and a finger mount on a second end of the stem for mounting the tem on a finger with the stem projecting from the end of the finger.

Preferably, the elongate stem has two parts at an oblique angle to one another. One part extends from the finger mount, generally parallel to the finger to a position past the end of the finger, while the second part slopes across the end of the finger to place the lens at a comfortable position in relation to the finger end for insertion. The preferred insertion position is with the finger pointing at a position slightly to one side of and below the pupil. Thus, the preferred position of the lens retainer is in front of and above the fingertip. This allows the user to employ the other fingers of the hand carrying the lens for holding open the eyelid.

The lens is not supported on the finger and therefore is not contaminated by finger contact.

The finger mount may be either integral with the stem or may be separate from the stem and include means for attaching it to the stem.

BRIEF DESCRIPTION OF THE DRAWINGS

In the accompanying drawings, which illustrate an exemplary embodiment of the present invention.

DETAILED DESCRIPTION

Figure 1:
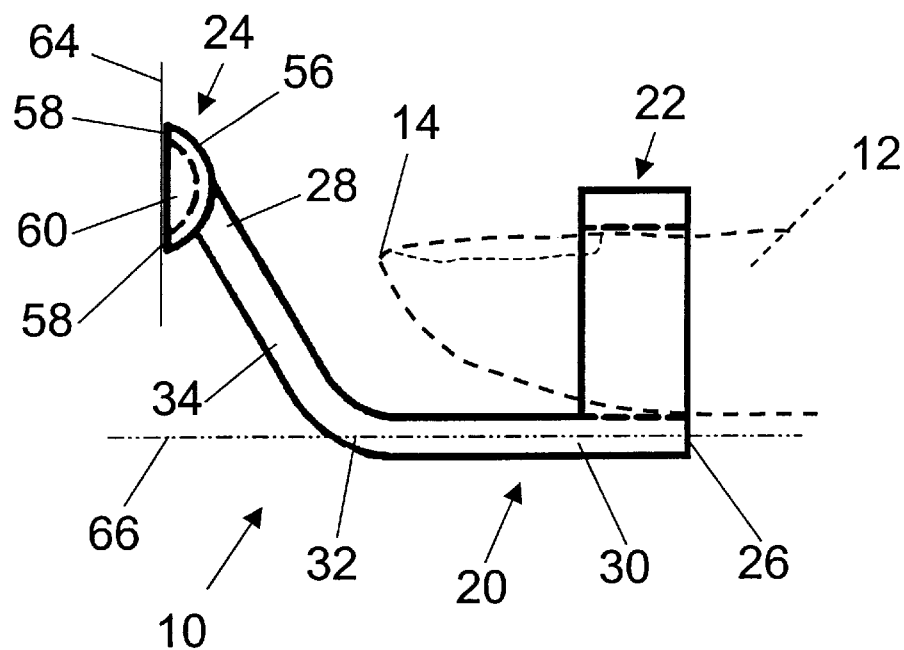
FIG. 1 is a side view of the contact lens applicator.
Figure 2:
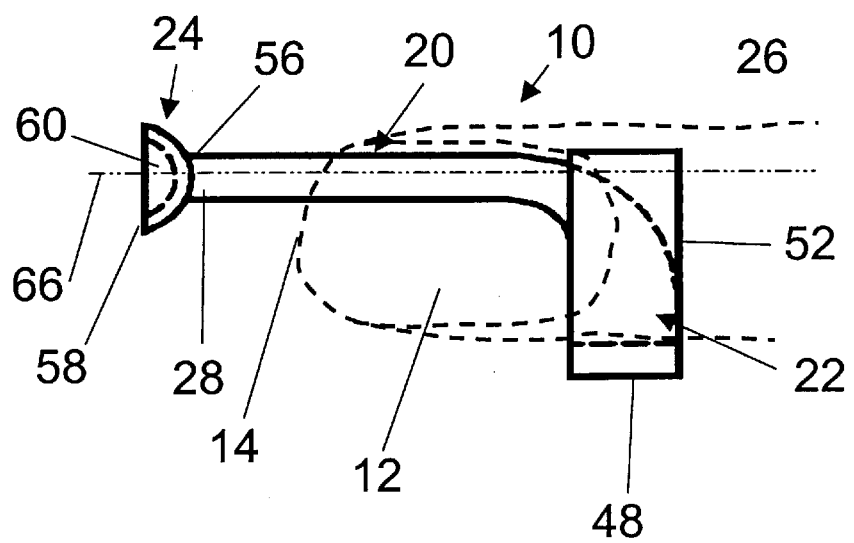
FIG. 2 is a top view of the contact lens applicator.
Figure 3:
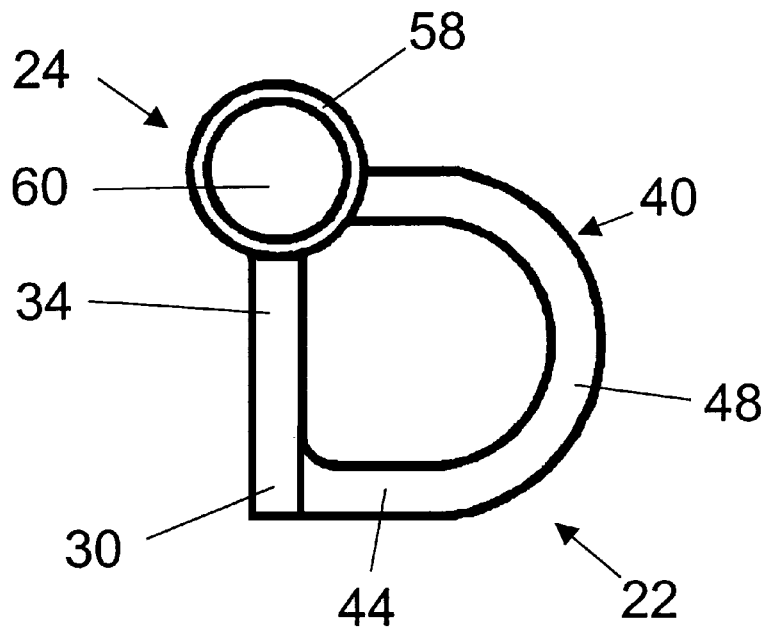
FIG. 3 is a front view of the contact lens applicator.
Figure 4:
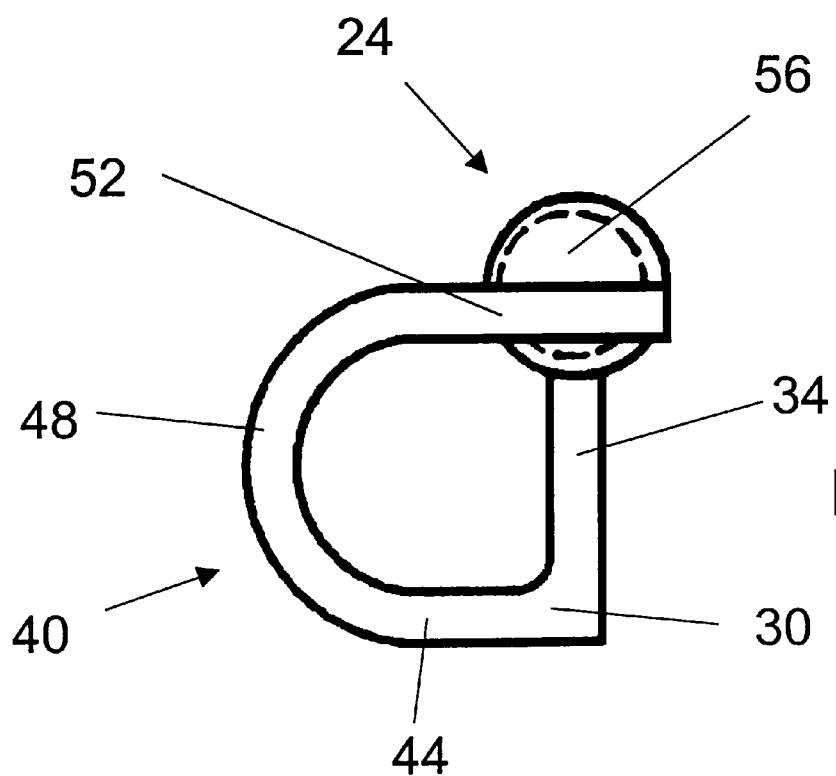
FIG. 4 is a rear view of the contact lens applicator.
Figure 6:
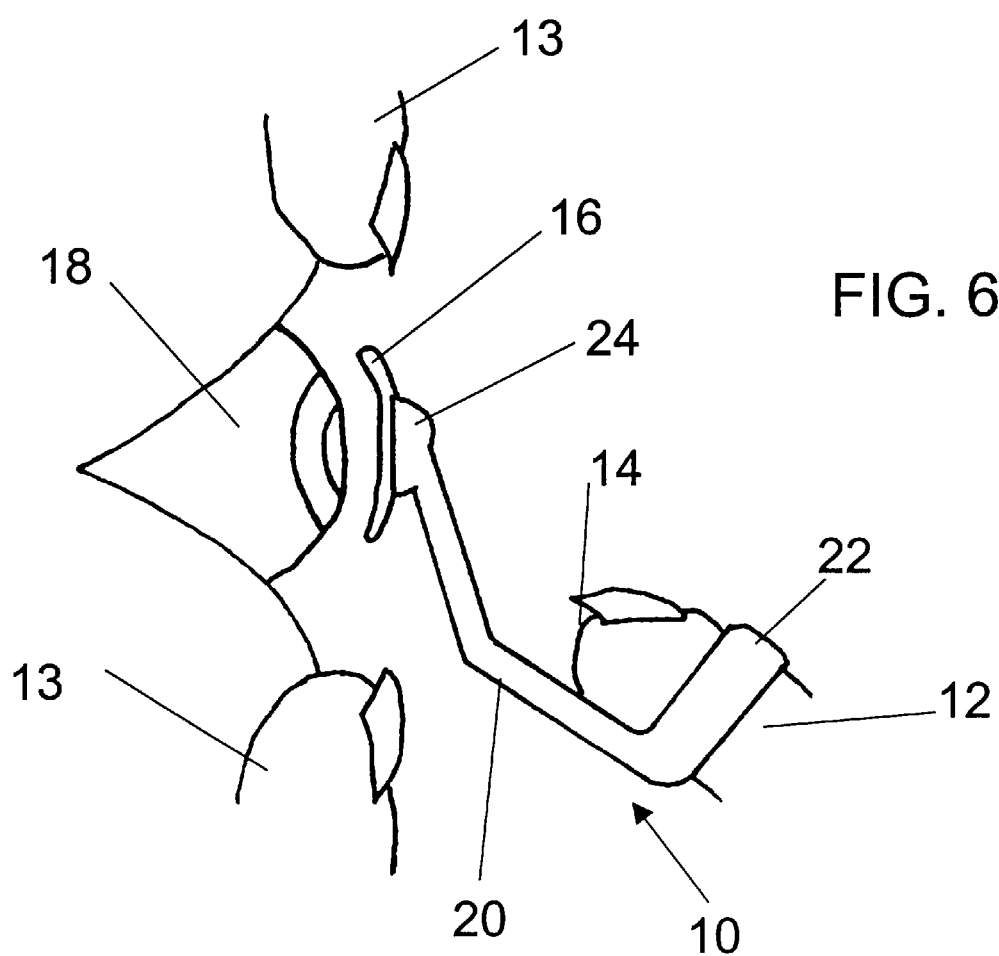
FIG. 6 is a side view showing the contact lens applicator in use and in place on a finger with a contact lens in place on the applicator.

Referring to the drawings, and especially to FIGS. 1, 2 and 6, a contact lens applicator 10 is placed on a finger 12 adjacent the fingertip 14 and is used to apply a contact lens 16 to an eye 18. The contact lens applicator 10 includes an elongate stem 20, a finger mount 22, and a contact lens retainer 24.

The stem 20 has a mounting end 26 and an outer, lens retainer end 28. A first part 30 of the stem extends from the mounting end, parallel to the finger, to a position spaced beyond the end 14 of the finger. At its outer end, the stem part 30 merges through an oblique angle 32 (approximately 120°) into a second part 34 that extends to the retainer end 28 of the stem 20. The retainer end 28 of the stem 20 lies beyond the end of, and above and to one side of the fingertip 14.

Referring to FIGS. 1 to 4, the finger mount 22 is attached to the mounting end 26 of the stem 20 and engages around a portion of the finger 12 adjacent the fingertip 14. The finger mount 22 is a generally C-shaped member 40 having a lower arm 44, a curved portion 48, and an upper arm 52. The C-shaped member 40 is attached to the stem 20 at the end 42 of the lower arm 44. It projects to one side of and is perpendicular to the stem 20. The C-shaped member 40 merges into the curved portion 48, which in turn merges into the upper arm 52. The upper arm 52 is longer than the lower arm and extends past the stem 20.

To mount the applicator 10 on a finger, the finger 12 is placed within the partial loop formed by the C-shaped member 40. The C-shaped member 40 is sized to fit snugly upon a finger of most individuals and will be held in place on the finger by friction.

Since the finger mount 22 extends to one side of the stem 20, the finger 12 lies slightly to one side of the stem 20, thereby positioning the lens retainer end 28 of the stem 20 to one side of the finger 12.

Referring to FIGS. 1 to 4, the contact lens retainer 24 is fixed to the end 28 of the stem 20. It is a shallow cup shaped member 56 having a circular rim 58 surrounding a cavity 60. The retainer is used to hold the contact lens 16 on the end of the stem 20. The member 56 extends transversely across the end of the stem and is oriented with the rim 58 generally perpendicular to a longitudinal axis 66 of the first part 30 of the stem 20.

Figure 5:
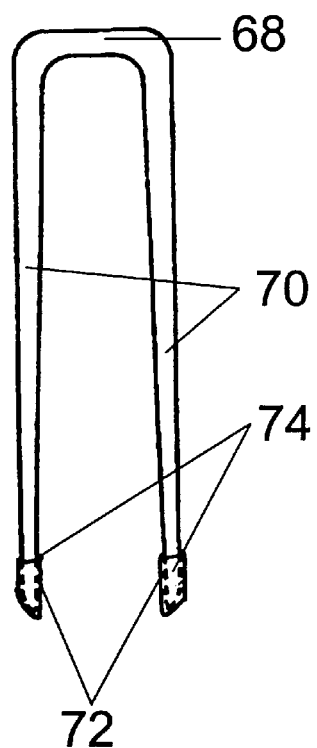
FIG. 5 is a front view of a pair of tweezers for use with the contact lens applicator.

Referring to FIGS. 5 and 6, tweezers 68 are employed to place the contact lens 16 on the retainer 24. The tweezers 68 allow an individual to place the contact lens 16 on the contact lens applicator 10 without touching the contact lens 16, thereby preventing dirt or oils on the fingers from getting on the contact lens 16. The tweezers 68 include a pair of arms 70 each having a contact surface 72 arranged at end thereof, and padding means 74 arranged on the contact surface 72. The padding means 74 are silicone sleeves, one being arranged to extend over and around each end and across a respective contact surface 72. The padding means 74 help prevent damage to the contact lens 16 during placement of the contact lens 16 on the contact lens applicator 10.

In use the contact lens applicator 10 is placed on the finger 12 of one hand, adjacent the fingertip 14, and a sterile fluid such as saline is placed on the cup shaped member 56 of the retainer 24. During this process the cup shaped member 56 is arranged such that rim 58 faces upwards thereby retaining the wetting fluid on the surface of the cup shaped member 56. The tweezers 68 are then used to pick up the contact lens 16 and place the contact lens 16 on the contact lens retainer 24 such that an exterior convex portion of the contact lens 16 is in contact with the rim 58 of the contact lens retainer 24 and in contact with the wetted surface of the retainer 24. The contact lens 16 is oriented such that the inner concave portion which is to contact the eye 18 faces away from the contact lens retainer 24. The fluid on the cup 56 of the retainer 24 holds the contact lens 16 in place on the retainer 24 with sufficient force that the contact lens 16 remains on the retainer 24 when the applicator 10 is moved into a position with the rim 58 and the lens oriented substantially vertically. This allows the user to orient the finger 12 substantially horizontally with the contact lens 16 extending forward of the fingertip 14.

The eye 18 receiving the contact lens is held open using the fingers of the hand without the applicator 10 and the remaining fingers of the hand with the applicator 10. The user may then move the finger 12 having the applicator 10 towards the eye 18 carefully positioning the contact lens 16 until it contacts the eye 18. The contact lens applicator 10 and finger 12 are then moved away from the eye 18 leaving the contact lens 16 behind in place on the eye 18.

It is easier for a novice to place a contact lens in an eye using the contact lens applicator 10 since the contact lens applicator 10 is positioned on the end of a finger 12 of one hand and can hold the contact lens 16 in place on the finger 12 even when the applicator 10 is in a horizontal position. Since the contact lens applicator 10 is mounted on only one finger, usually the middle finger, the other fingers of that hand are free to help hold the eyelids open. Also, since the contact lens 16 can be retained on the contact lens applicator 10 even in a vertical orientation, it is easy to make use of a vertical mirror if desired. Furthermore, having the contact lens retainer 24 positioned above and slightly to one side of the finger 12 allows the individual to more easily see the contact lens as it approaches the eye 18, and reduces the problems associated with the image of the finger 12 interfering with the image of the contact lens 16.

In an alternative embodiment, the finger mount 22 may comprise any other appropriate means for mounting the contact lens applicator 10 to the finger 12. Some examples of alternative finger mount are a ring, a strap, an elastic loop, or an adhesive.

In another alternative, the finger mount 22 may be separate from the stem 20 and may include attachment means for connecting it to the stem 20 adjacent the mounting end 26.

It is to be understood that the second part 34 of the stem 20 may be placed at any appropriate angle to the first part 30 of the stem 20 which would place the retainer end 28 of the stem 20 upwards and to one side of the fingertip 14.

While certain embodiments of the present invention have been described in the foregoing, it is to be understood that other embodiments are possible within the scope of the invention. The invention is to be considered limited solely by the scope of the appended claims.

I claim:

1. A contact lens applicator for applying a contact lens to an eye of a person using a finger of the person, said finger having a fingertip, said contact lens applicator comprising:

an elongate stem:

a contact lens retaining means on a first end of the stem for retaining a contact lens on the end of the stem, with the lens transverse to the stem end: and a finger mount on a second end of the stem for mounting the stem on the finger with the stem positioned to one side of the finger and projecting from the end of the finger and with the retaining means positioned beyond the end of and offset to one side of and above the fingertip.

2. A contact lens applicator in accordance with claim 1 wherein the stem comprises a first part extending from the finger mount and a second part extending at an oblique angle from the first part to the retaining means.

3. A contact lens applicator in accordance with claim 2 wherein the contact lens retaining means comprises a cup shaped member fixed to the first end of the stem and facing away from the stem.

4. A contact lens applicator in accordance with claim 3 wherein the cup shaped member has a rim lying in a plane substantially perpendicular to a longitudinal axis of the first part of the stem.

5. A contact lens applicator in accordance with claim 1 wherein the finger mount comprises a curved member attached to the stem for engaging around a portion of the finger near the fingertip.

6. A contact lens applicator in accordance with claim 5 wherein the finger mount is integral with the stem.

* * * * *